United States Patent [19]

Vlattas

[11] Patent Number: 4,665,087
[45] Date of Patent: May 12, 1987

[54] 1-(CARBAMYL, THIOCARBAMYL, AND IMINOCARBAMYL)-INDOLINE DERIVATIVES

[75] Inventor: Isidoros Vlattas, Summit, N.J.

[73] Assignee: Ciba-Geigy Corporation, Ardsley, N.Y.

[21] Appl. No.: 772,793

[22] Filed: Sep. 5, 1985

Related U.S. Application Data

[63] Continuation of Ser. No. 350,694, Feb. 22, 1982, abandoned.

[51] Int. Cl.$^4$ .................. A61K 31/405; C07D 209/26
[52] U.S. Cl. ..................................... 514/419; 548/491; 548/492; 548/430
[58] Field of Search .................. 548/491; 514/419

[56] References Cited

U.S. PATENT DOCUMENTS

| | | | |
|---|---|---|---|
| 3,780,062 | 12/1973 | Kaiser et al. | 548/491 |
| 3,796,723 | 3/1974 | Kaiser et al. | 548/491 |
| 4,179,434 | 12/1979 | Ondetti et al. | 260/112.5 R |
| 4,256,751 | 3/1981 | Hayashi et al. | 546/147 |
| 4,294,832 | 10/1981 | Yoneda et al. | 514/307 |
| 4,303,583 | 12/1981 | Kim et al. | 548/414 |
| 4,344,949 | 8/1982 | Hoefle et al. | 548/178 |
| 4,350,704 | 9/1982 | Hoefle et al. | 546/170 |
| 4,374,829 | 2/1983 | Harris et al. | 260/112.5 R |
| 4,374,847 | 2/1983 | Gruenfeld | 548/491 |
| 4,390,700 | 6/1983 | Stanton et al. | 546/165 |
| 4,402,969 | 9/1983 | Greenlee et al. | 424/274 |
| 4,404,206 | 9/1983 | Vincent et al. | 548/492 |
| 4,515,803 | 5/1985 | Henning et al. | 548/455 |

FOREIGN PATENT DOCUMENTS 2470767 12/1981 France ............................. 548/450

OTHER PUBLICATIONS

Derwent Abstract 836003 of Japan 5-8185-565, published Oct. 29, 1983.

Primary Examiner—Mark L. Berch
Assistant Examiner—G. Hendricks
Attorney, Agent, or Firm—Norbert Gruenfeld

[57] ABSTRACT

1-(Carbamyl, thiocarbamyl, and iminocarbamyl)-indoline derivatives of the formula

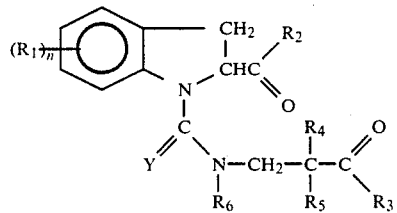

where each $R_1$ is independently alkyl, alkoxy, acyloxy, hydroxy, halo or trifluoromethyl, n is 0, 1, 2 or 3, $R_2$ and $R_3$ are independently hydroxy, alkoxy, amino or substituted amino, $R_4$ and $R_5$ are independently hydrogen, alkyl or substituted alkyl, $R_6$ is hydrogen, alkyl or substituted alkyl, and Y is O, S or N—$R_7$ where $R_7$ is hydrogen, alkyl, cyano or substituted alkyl, and salts thereof, which are useful as antihypertensive and cardioactive agents, methods of preparing the same, and pharmaceutical compositions thereof, are provided.

9 Claims, No Drawings

1-(CARBAMYL, THIOCARBAMYL, AND IMINOCARBAMYL)-INDOLINE DERIVATIVES

CROSS REFERENCE TO RELATED APPLICATIONS

This is a continuation of application Ser. No. 350,694 filed Feb. 22, 1982, now abandoned.

SUMMARY OF THE INVENTION

It is an object of the invention to provide new 1-(carbamyl, thiocarbamyl, and iminocarbamyl)-indoline derivatives of the formula

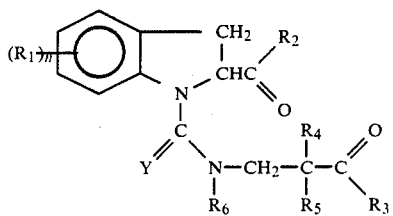

where each $R_1$ is independently alkyl, alkoxy, acyloxy, hydroxy, halo, trifluoromethyl or two adjacent $R_1$ taken together represent alkylenedioxy; n is 0, 1, 2 or 3; $R_2$ and $R_3$ are independently hydroxy, alkoxy, or substituted alkoxy, amino or substituted amino; $R_4$ and $R_5$ are independently hydrogen, alkyl or substituted alkyl; $R_6$ is hydrogen, alkyl or substituted alkyl; and Y is O, S or N-$R_7$ where $R_7$ is hydrogen, alkyl, cyano or substituted alkyl; and salts thereof.

It is a further object of the invention to provide methods for preparing the compounds of formula I.

It is a further object of the invention to provide a method of treating cardiovascular diseases such as hypertension or congestive heart failure in mammals, which consists of administering, alone or in combination, to mammals in need thereof, an effective amount of the compound of formula I.

It is a further object of the invention to provide pharmaceutical compositions, preferably an antihypertensive and cardioactive pharmaceutical composition comprising a compound of formula I, together with a pharmaceutical excipient.

DETAILED DESCRIPTION OF THE INVENTION

A preferred embodiment of the compounds of formula I are those wherein each $R_1$ independently represents lower alkyl, lower alkoxy, lower alkanoyloxy, hydroxy, halo, or trifluoromethyl, or two adjacent substituents $R_1$ taken together may additionally represent lower alkylenedioxy;

n is 0, 1, 2 or 3;

$R_2$ and $R_3$ independently represent hydroxy, lower alkoxy, (aryl, lower alkanoyloxy, amino, mono- or di-loweralkylamino, carboxy, or lower alkoxycarbonyl) lower alkoxy; amino, lower alkylamino, or di-lower alkylamino;

$R_4$ and $R_5$ independently represent hydrogen, lower alkyl, or lower alkyl substituted by aryl or by heteroaryl;

$R_6$ is hydrogen, lower alkyl or lower alkyl substituted by amino, lower alkylamino, di-lower alkylamino, lower alkanoylamino, aroylamino, aryl-lower alkylamino, aryl-lower alkoxycarbonylamino, hydroxy, carboxy, lower alkoxycarbonyl, lower alkanoyloxy, aminocarbonyl, lower alkylaminocarbonyl, di-lower alkylaminocarbonyl, aryl or by heteroaryl;

Y is O, S or N-$R_7$, where $R_7$ is hydrogen, cyano, lower alkyl or lower alkyl substituted by aryl;

and salts, particularly pharmaceutically acceptable salts thereof.

The term, "lower", referred to above and hereinafter in connection with organic radicals and compounds, respectively, defines such with up to 7, preferably 4, and advantageously one or two, carbon atoms.

Thus, the expression, "lower alkyl", as used herein includes both straight and branched chain alkyl groups, including, inter alia, the following: methyl, ethyl, n-propyl, i-propyl, n-butyl, i-butyl, n-pentyl, n-hexyl, n-heptyl, and the like.

The term "lower alkyl substituted by aryl" represents preferably phenylethyl, benzyl and the like optionally substituted on the phenyl ring like "phenyl" in the term "aryl".

Likewise, the expression, "lower alkoxy", as used herein, includes both straight and branched chain alkoxy groups, of up to 7 carbon atoms including, for example, methoxy, ethoxy, n-propoxy, i-propoxy, n-butoxy, i-butoxy, n-pentyloxy, 1-methylbutoxy, 2-methylbutoxy, and the like.

The term "lower alkoxycarbonyl" represents preferably methoxycarbonyl, ethoxycarbonyl and the like.

The term "aryl lower alkoxy" represents preferably e.g., benzyloxy.

The term "lower alkanoyloxy lower alkoxy" represents preferably lower alkanoyloxymethoxy, e.g., pivaloyloxymethoxy.

The term "lower alkoxycarbonyl lower alkoxy "represents preferably e.g. 1-(ethoxycarbonyl)ethoxy.

The expression, "lower alkylamino", includes the corresponding straight and branched chain alkyl amino groups, such as methylamino, ethylamino, n-propylamino or isopropylamino.

Di-lower alkylamino groups include those wherein each alkyl group contains up to 7 carbon atoms, such as N,N-dimethylamino, N,N-diethylamino, N-methyl-N-ethylamino, N-methyl-N-propylamino, N-methyl-N-isopropylamino, N,N-dipropylamino, N-ethyl-N-butylamino, N-methyl-N-heptylamino, and the like.

Lower alkylenedioxy includes methylenedioxy, 1,1- and 1,2-ethylenedioxy, and the like, of up to 7 carbon atoms.

The term, "lower alkanoyl", as in lower alkanoyloxy, and lower alkanoylamino, includes those moieties in which the acyl group contains up to 7 carbon atoms such as formyl, acetyl, propionyl, butyryl, isobutyryl and the like.

The term, "halo", preferably includes chloro, bromo and fluoro, but may also be iodo.

The term "aryl" as used herein, preferably includes phenyl and phenyl substituted by one to three of lower alkyl, lower alkoxy, hydroxy, lower alkanoyloxy, halo, or trifluoromethyl; advantageously o-, m- and p-tolyl, o-, m- and p-methoxyphenyl, o-, m- and p-chlorophenyl and especially phenyl.

The term "heteroaryl" represents, preferably e.g. 1- or 4-imidazolyl.

The term "aroyl" as in aroylamino preferably includes benzoyl and benzoyl substituted on the phenyl ring like "phenyl" in the term "aryl".

The term "aryl-lower alkanoylamino" represents preferably phenylacetylamino, phenylpropionylamino, and the like.

The term "aryl-lower alkoxycarbonylamino" represents preferably carbobenzyloxyamino and carbobenzyloxyamino substituted on the phenyl ring like "phenyl" in the term "aryl".

The term "aryl-lower alkylamino" represents preferably benzylamino or benzylamino substituted on the phenyl ring like "phenyl" in the term "aryl".

Those compounds of formula I in which there is a free acid group, for example, where either or both of $R_2$ and $R_3$ are hydroxy, or where $R_6$ is lower alkyl substituted by carboxy, form salts, particularly pharmaceutically acceptable salts with bases. Any conventional base can be utilized to form a salt in accordance with this invention.

Pharmaceutically acceptable salts are preferably metal or ammonium salts of said acids, more particularly alkali or alkaline earth metal salts, for example, the sodium, potassium, magnesium or calcium salt; or ammonium salts of ammonia or organic amines, such as mono-, di- or tri-lower (alkyl or hydroxyalkyl)-amines, such as methylamine, dimethylamine, diethylamine, diethanolamine, triethanolamine, ethylamine, tris(hydroxymethyl)-aminomethane and the like; mono- or di-(cycloalkyl) amines, such as cyclohexylamine and dicyclohexylamine; lower alkylenediamines, such as ethylenediamine; heterocyclic amines, such as morpholine; aryl-lower alkyl-amines, such as benzylamine and phenethylamine; and quaternary ammonium derivatives thereof, such as benzyl-trimethylammonium hydroxide.

In addition, the compounds of formula I in which there is a basic nitrogenous group, for example, where $R_6$ is lower alkyl substituted by amino, lower alkylamino or di-lower alkylamino, or where Y is N-$R_7$, or both, form salts, particularly pharmaceutically acceptable salts with acids. Any conventional acid can be utilized to form a salt in accordance with this invention.

Suitable acids include inorganic and organic acids, including hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, gluconic, nicotinic, methanesulfonic, ethanesulfonic, halobenzenesulfonic, toluenesulfonic, naphthalenesulfonic, sulfanilic or cyclohexylsulfamic acid. Salts may also be formed with amino acids, such as arginine and lysine.

If several acid or basic groups are present, mono- or poly-salts may be formed.

Compounds of the formula I having an acidic, for example a free carboxyl, group and basic, for example amino, group may also be in the form of internal salts, i.e. in zwitterion form, or one part of the molecule may be in the form of an internal salt and another may be in the form of a normal salt.

It is also possible to use pharmaceutically unacceptable salts for isolation or purification. Only pharmaceutically acceptable salts are used therapeutically and these are therefore preferred.

In addition to the pharmaceutically acceptable salts cited above, any prodrug derivatives, e.g., pharmaceutically acceptable esters and amides of the carboxylic acids of this invention that may be convertible by solvolysis or under physiological conditions to the said carboxylic acids, represent a further object of this invention.

Said esters are preferably e.g., the straight chain or branched lower alkyl esters unsubstituted or suitably substituted such as the pivaloyloxymethyl, 2-diethylaminoethyl, α-carboxyethyl or suitably esterified α-carboxyethyl esters and the like which are prepared by methods well known to the art.

Said amides are preferably e.g. simple primary and secondary amides and the amides derived from the amino acids or derivatives thereof, such as the amides derived from alanine, phenylalanine and the like.

In a more preferred embodiment of the compounds of formula I, each $R_1$ independently represents lower alkyl particularly methyl or ethyl; lower alkoxy, particularly methoxy or ethoxy; lower alkanoyloxy particularly acetoxy; hydroxy; halogen particularly chloro; or two adjacent $R_1$ taken together represent particularly methylenedioxy, or 1,1- or 1,2-ethylenedioxy; n is 0, 1 or 2; $R_4$ is hydrogen; $R_5$ is lower alkyl, lower alkyl substituted by phenyl; $R_6$ is hydrogen, lower alkyl, or lower alkyl substituted by amino, lower alkylamino, di-lower alkylamino, hydroxy or by phenyl; $R_2$ and $R_3$ are as defined above; and salts, particularly pharmaceutically acceptable salts thereof.

Especially preferred are those compounds of formula I, and advantageously those in the preferred embodiment set forth in the previous paragraph, which are in the form of the indoline-2S-chiral epimers thereof.

Especially valuable are the compounds of formula II

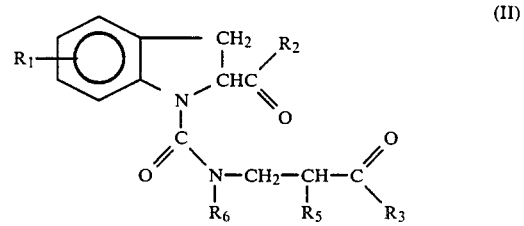

preferably the indoline-2S-chiral epimers thereof, wherein $R_1$ is hydrogen, lower alkyl, hydroxy, lower alkanoyloxy, lower alkoxy, halo or trifluoromethyl; $R_2$ and $R_3$ are independently hydroxy, lower alkoxy or amino; $R_5$ is hydrogen, lower alkyl, alkyl of 1 to 4 carbon atoms substituted by phenyl or by $R_8$-phenyl wherein $R_8$ represents lower alkoxy, lower alkyl, halo or trifluoromethyl; $R_6$ is lower alkyl, or lower alkyl substituted by hydroxy, amino, lower alkylamino or by di-lower alkylamino; and salts, particularly pharmaceutically acceptable salts thereof.

Especially advantageous are the indoline-2-S-chiral epimers of the compounds of formula II wherein $R_2$ and $R_3$ are independently hydroxy, alkoxy of 1 to 4 carbon atoms or amino; $R_5$ is alkyl of 1 to 4 carbon atoms, or alkyl of 1 to 4 carbon atoms substituted by phenyl; $R_6$ is alkyl of 1 to 4 carbon atoms, or alkyl of 2 to 7 carbon atoms substituted by hydroxy, amino, alkylamino of 1 to 4 carbon atoms or by di-alkylamino wherein each alkyl has 1 to 4 carbon atoms; and salts, particularly pharmaceutically acceptable salts thereof.

In the above compounds of formula (I) or (II), in addition to the optically active center at the carbon atom in the 2-position of the indoline ring, the carbon atom to which the $R_5$ group is attached may also be an optically active center.

One advantageous embodiment of the indoline-2S-chiral epimers of the compounds of formula (I) are those wherein $R_4$ is hydrogen and the carbon atom to which $R_5$ is attached is in the (R) configuration when $R_5$ is alkyl or substituted alkyl.

Similarly advantageous are the indoline-2S-chiral epimers of formula II wherein the carbon atom to which $R_5$ is attached is in the (R)-configuration when $R_5$ is lower alkyl, preferably alkyl of 1 to 4 carbon atoms, or alkyl of 1 to 4 carbon atoms substituted by phenyl or by $R_8$-phenyl.

Most preferred are such compounds of formula II, wherein $R_5$ is phenethyl, said carbon atom to which $R_5$ is attached is in the (R)- configuration, $R_1$ is hydrogen, $R_2$ and $R_3$ are independently hydroxy or alkoxy of 1 to 4 carbon atoms, and $R_6$ represents alkyl of 1 to 4 carbon atoms or alkyl of 2 to 4 carbon atoms substituted by amino or by hydroxy.

The compounds of this invention exhibit valuable pharmacological e.g., cardiovascular properties, primarily hypotensive, antihypertensive and cardioactive effects, inter alia, due to their angiotensin converting enzyme inhibitory activity. These are demonstrable by in vivo or in vitro animal tests, using advantageously mammals, e.g., rats, cats, dogs or isolated organs thereof, as test objects. The animals may either be normotensive or hypertensive e.g., genetically hypertensive rats, or renal hypertensive rats and dogs, and sodium-depleted dogs. Said compounds can be applied to them enterally or parenterally, advantageously orally or intravenously, for example within gelatin capsules or in the form of starchy suspensions or aqueous solutions respectively. The applied dosage may range between about 0.01 and 50 mg/kg/day, preferably between about 0.05 and 40 mg/kg/day, advantageously between about 0.1 and 30 mg/kg/day.

The in vivo lowering effect on the blood pressure is recorded either directly by means of a catheter, for example placed in the dog's femoral artery, or indirectly by sphygmomanometry at the rat's tail, and a transducer, expressing the blood pressure prior and after dosing in mm Hg. Thus, for example, the representative members of the compounds of this invention, illustrated by the Examples herein, are very effective in hypertensive rats and dogs at p.o.-doses as low or lower than 30 mg/kg/day.

Thus the antihypertensive effects are demonstrable in spontaneous hypertensive rats by indirect measurement of systolic pressure. Conscious rats are placed individually in restraint cages within a gently warmed chamber. A rubber pulse sensor is placed distal to an inflatable occlusive cuff on each rat's tail. The cuff is periodically inflated to occlude the tail artery, and systolic pressure is recorded as the point where the first discernible pulse emerges along the decaying calibrated pressure curve. After obtaining control values of blood pressure and heart rate, test compounds are administered orally once daily for 4 consecutive days. Additional blood pressure measurements are usually made at 2.0, 4.0 and 23.5 hours after each daily dosing, and responses are compared to those of rats dosed with the treatment vehicle.

The compounds also exhibit an inhibitory effect against the angiotensin I pressure response of normotensive rats. The enzyme renin normally causes specific hydrolysis of the circulating protein renin substrate. This hydrolysis generates angiotensin I, which is further hydrolyzed by the action of said converting enzyme to the potent vasoconstrictor angiotensin II. The inhibition of said enzyme prevents the generation of angiotensin II from I and, therefore, attenuates any pressure response following an angiotensin I challenge.

The corresponding in vivo test is performed with male, normotensive rats, which are anesthetized with 100–120 mg/kg i.p. of sodium ethyl-(1-methylpropyl)-malonylthiourea. A femoral artery and saphenous vein are cannulated for direct blood pressure measurement and i.v. administration of angiotensin I and compounds of this invention. After the basal blood pressure is stabilized, pressor response is to 3 challenge of 0.33 $\mu$g/kg of angiotensin I i.v., in 5 minutes intervals, are obtained. Such pressure responses are again obtained 5, 10, 15, 30 and 60 minutes after either i.v., or p.o. administration (stomach tube) of the compounds to be tested, and compared with the initial responses. The observed decrease of said pressor response on administration of a compond of this invention is an indication of angiotensin I converting enzyme inhibition, and ranges up to 100% after doses as low or lower than 1 mg/kg i.v. or up to 50% or better at doses of 10 mg/kg p.o, which decrease may be sustained up to 60 minutes.

The in vitro inhibition of the angiotensin-converting enzyme by the compounds of this invention can be demonstrated analogous to Biochim. Biophys. Acta 293, 451 (1973). According to this method said compounds are dissolved at about 1 mM concentrations in phosphate buffer, externally cooled with ice. To these solutions various $\mu$l amounts of 1 mM of histidyl-leucine in phosphate buffer are added, followed by 100 $\mu$l of 4mM hippuryl-histidyl-leucine in phosphate buffer and 50 $\mu$l of the angiotensin-converting enzyme, which is freshly prepared from lungs of adult male rabbits in Tris buffer, containing potassium and magnesium chloride, as well as sucrose. The solutions are incubated at 37° C. for 30 minutes and combined with 0.75 ml or 0.6 N aqueous sodium hydroxide to stop further reaction. Then 100 $\mu$l of o-phthalaldehyde are added at room temperature, and 10 minutes later 100 $\mu$l of 6N hydrochloric acid. These samples are read against water in a spectrophotometer set at 360 nm, and the optical densities thereof estimated. They are corrected for the standard curve via a conversion factor expressing nanomoles of histidyl-leucine formed during the 30 minute incubation period. The results are plotted against drug concentration to determine the $IC_{50}$, i.e., the drug concentration which gives half the activity of the control sample containing no drug. Again, representative members of the compounds of this invention are very effective in this in vitro test system, down to $IC_{50}$ values as low as 5 nM ($5 \times 10^{-9}$M).

Illustrative of the compounds of this invention, the compound of example 9, namely 1S-[(R)-N-(2-carboxy-4-phenylbutyl)-N-(4-aminobutyl)carbamoyl]-2,3-dihydroindole-2-carboxylic acid disodium salt, with an $IC_{50}$ of about $6 \times 10^{-9}$M for inhibition of angiotensin-converting enzyme, virtually completely inhibits the angiotensin I induced hypertension in the rat at a dose of 1.0 mg/kg i.v.

Accordingly, the compounds of this invention are valuable cardiovascular agents, especially useful in mammals for ameliorating hypertension (regardless of etiology) and/or heart-conditions, such as congestive heart failure, and/or other edemic or ascitic diseases, e.g. hepatic cirrhosis. They are also useful intermediates in the preparation of other valuable products, especially of corresponding pharmaceutical compositions.

The compounds of formula I are advantageously prepared according to processes 1 and 2.

(1) reacting a compound of formula III

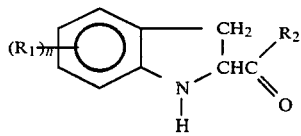

with a reactive functional derivative of a compound of formula IV

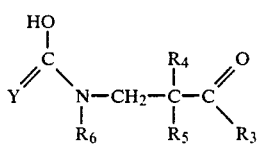

in which optionally present functional groups in $R_1$–$R_6$ may be in protected form.

(2) reacting a reactive functional derivative of compound of formula V

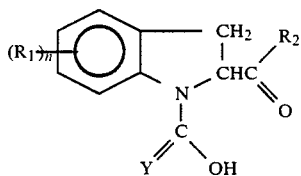

with a compound of the formula VI

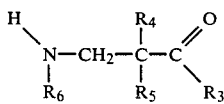

in which optionally present functional groups in $R_1$–$R_6$ may be in protected form.

The compound of formula I may also be prepared according to processes 3 to 5.

(3) Reacting a compound of the formula VII

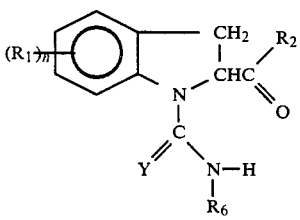

or the N-alkali metal derivative thereof, with a compound of the formula VIII;

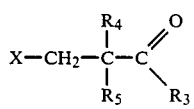

where X is a reactive esterified hydroxy group, such as halo, arylsulfonyloxy or alkylsulfonyloxy, and in which optionally present functional groups in $R_1$–$R_6$ may be in protected form, and optionally converting any resulting compound into another compound of formula I.

(4) Reducing a compound of the formula IX,

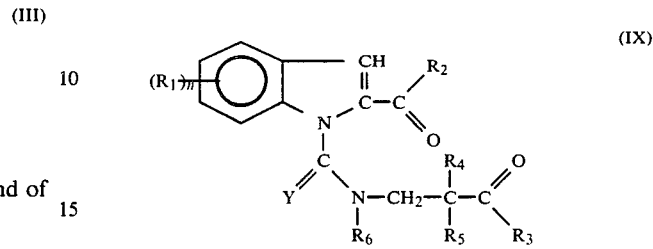

specifically the 2,3-double bond in the indole moiety, wherein the optionally present functional groups in $R_1$–$R_6$ may be in protected form;

(5) Hydrolyzing or alcoholyzing a compound of the formula XII

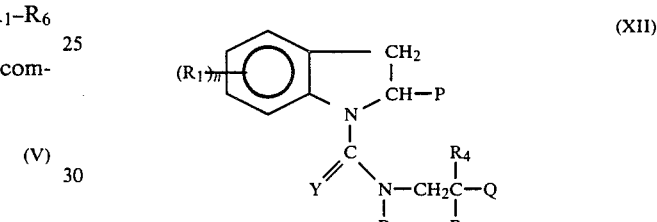

wherein at least one of P and Q is cyano, and the other may be $COR_2$ or $COR_3$ as defined for formula I.

Also included within the above processes 1 to 5 are:

(a) converting any protected functional group in a resulting compound prepared according to the above processes 1 to 5 into the free functional group; and/or (b) if desired, converting salt into the free compound, and/or converting a resulting compound having a salt-forming group into a salt, and/or if desired, (c) separating any resulting mixture of isomeric compounds into the single isomers; and/or if desired, (d) converting any resulting compound prepared according to the above processes 1 to 5 into any other compound of this invention;

Reactive function-al derivatives of compounds IV are those in which the group

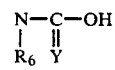

is in the form of preferably the N-carbonyl halides, especially chlorides such as the corresponding carbonyl or thiocarbonyl chloride; the N-nitriles, N-lower alkyl esters, lower alkyl thioesters, lower alkyl imino ethers and lower alkyl imino thioethers; and where $R_6$ is hydrogen, the corresponding isocyanates and isothiocyanates. The reaction of compounds III and the functional derivatives of IV occurs either spontaneously or in the presence of suitable conventional condensation agents, such as bases, including advantageously tertiary amines such as triethylamine, pyridine and the like, especially where the functional derivatives of compounds IV are in the form of their acid chlorides, isocyanates and isothiocyanates. Advantageously, the reaction is conducted in the presence of an inert solvent or diluent, such as benzene, toluene, tetrahydrofuran, or dimethylformamide, at a temperature of between about −20° to 100° C., optionally under a nitrogen atmosphere.

Similarly, the reactive functional derivatives of compounds V are preferably the N-carbonyl halides, such as the corresponding carbonyl or thiocarbonyl halides, the corresponding N-nitriles, or the corresponding N-lower alkyl imino ethers and lower alkyl imino thioethers. The reaction of the functional derivatives of compound V and compound VI takes place either spontaneously or in the presence of suitable conventional condensation agents, e.g. tertiary amines. Conveniently, the reaction is conducted in the presence of an inert solvent or diluent, such as benzene, toluene, tetrahydrofuran or dimethylformamide at a temperature of between about −20° to 100° C., optionally under a nitrogen atmosphere.

The reaction of the compounds of formula VII, or the alkali metal derivatives thereof obtained by treatment with e.g. sodium hydride, with the compounds of formula VIII, is preferably performed under anhydrous conditions, optionally in the presence of an inert solvent or diluent, such as benzene, cyclohexane, toluene, diethylether, or dioxane at a temperature between about −20° to 100° C., advantageously in an inert atmosphere, e.g. nitrogen.

The reduction of the indoles of formula IX to the indolines of formula I is conducted according to conventional reductions of 1-acyl-indoles, for example, with catalytically activated or nascent hydrogen. Also reducing agents may be used, such as simple or complex light metal hydrides, such as boranes or alkali metal borohydrides or cyanoborohydrides. Preferred is asymmetric hydrogenation to the indoline-2S-derivatives with chiral catalysts, as, for example, prepared from a rhodium salt with (R)-1,2-bis-(diphenyl-phosphino)-propane or (R)-1,2-bis(o-anisylphenylphosphino)-ethane and 1,5-cyclooctadiene. Again the reaction is advantageously conducted in the presence of an inert diluent or solvent, such as cyclohexane, diethyl ether, dioxane, toluene or dimethylformamide at a temperature between about −20° to 100° C., optionally in an inert atmosphere, e.g. nitrogen.

The optional step of the conversion of a resulting product of formula I prepared according to the above processes into another compound of this invention are performed by chemical methodology known to the art and exemplified herein.

For example, compounds of formula I wherein $R_2$ and/or $R_3$ is lower alkoxy may be amidized with ammonia, mono- or di-(lower) alkylamines to yield compounds of formula I wherein $R_2$ and/or $R_3$ represents amino or substituted amino.

Conversion of compounds of formula I wherein $R_2$ and/or $R_3$ is alkoxy, substituted alkoxy, amino, or substituted amino to compounds of formula I wherein $R_2$ and/or $R_3$ represents hydroxy is advantageously carried out by hydrolysis with inorganic acids such as hydrohalic or sulfuric acid or with aqueous alkalies preferably alkali metal hydroxides such as lithium or sodium hydroxide.

The selective conversion of compounds of formula I wherein $R_2$ and/or $R_3$ represents aryl lower alkoxy, e.g. benzyloxy, to compounds of formula I wherein $R_2$ and/or $R_3$ represents hydroxy is advantageously carried out by hydrogenolysis using hydrogen in the presence of a catalyst e.g. palladium.

Compounds of formula I wherein neither $R_2$ nor $R_3$ represents hydroxy may be converted to monocarboxylic acids of formula I wherein one of $R_2$ and $R_3$ is hydroxy. Such conversion is carried out by selective hydrolytic or hydrogenolytic procedures well known to the art and based on the chemical character of the $R_2$ and $R_3$ substituents.

Free carboxylic acids of formula I wherein $R_2$ and/or $R_3$ represents hydroxy or salts thereof may be esterified with the appropriate alcohols or reactive derivatives thereof well known to the art to give the corresponding mono- or bis-ester, namely compounds of formula I wherein $R_2$ and/or $R_3$ is alkoxy or substituted alkoxy, e.g. aryl lower alkoxy. Furthermore the free carboxylic acids may be converted via reactive intermediates to mono- or bis-amides of formula I wherein $R_2$ and/or $R_3$ represents amino, or substituted amino, e.g. lower alkylamino or dilower alkylamino.

In the aforementioned methods for preparation of the compounds of the present invention, the optionally present functional groups may be advantageously present in protected form.

Thus, where one or more of $R_1$ is hydroxy, suitable protection may be afforded by conversion of the hydroxy group or groups into ester groups by replacement of the phenolic hydrogen by an easily split off acyl radical, such as lower alkanoyl, optionally substituted, for example by halo, such as 2,2-dichloroacetyl; or by acyl radicals of carbonic acid semiesters, such as tert-lower alkoxycarbonyl, or lower alkoxycarbonyl substituted in the 1-position by lower alkoxy or lower alkylthio, or optionally substituted diphenyl-methoxycarbonyl, or optionally substituted benzyloxycarbonyl, such as 4-nitrobenzyloxycarbonyl, or lower alkoxycarbonyl substituted in the 2-position by either an organosilyl group, such as 2-trimethylsilylethoxycarbonyl, or a tri lower alkylstannyl group, such as 2-trimethylstannylethoxycarbonyl, or by conversion of the hydroxy group into ether groups by replacement of the phenolic hydrogen by an easily split off etherifying group, such as the tert-lower alkyl, for example t-butyl, 2-oxa- or 2-thia-aliphatic or 2-oxa- or 2-thia-cycloaliphatic hydrocarbon radicals, such as 1-lower alkoxy-lower alkyl or 1-lower alkylthio-lower alkyl groups, for example methoxymethyl, 1-methylthioethyl, or 1-ethylthioethyl, or 2-oxa- or 2-thia-cycloalkyl having 5 to 7 ring atoms, for example 2-tetrahydrofuryl or 2-tetrahydropyranyl, and optionally substituted 1-phenyl-lower alkyl, such as optionally substituted benzyl or diphenylmethyl, suitable substituents of the phenyl radicals being, for example, halogen, such as chlorine, lower alkoxy, such as methoxy, lower alkyl, such as methyl, and /or nitro.

Likewise, when $R_6$ is lower alkyl substituted by hydroxy, the hydroxy group may be protected by the easily split off acyl radicals and etherifying groups set forth in the preceding paragraph.

Similarly, amino groups and mono-substituted amino groups, i.e. those optionally present in $R_6$ may also be protected by said easily split off acyl radicals.

Further acyl radicals to be considered as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, optionally substituted diph-enylphosphoryl, for example diphenylphosphoryl, di-phenyl-lower alkylphosphoryl optionally substituted, for example by nitro, for example dibenzylphosphoryl or di-4-nitrobenzylphosphoryl, optionally substituted phenoxyphenylphosphonyl, for example phenoxyphenylphosphonyl, di-lower alkylphosphinyl, for example diethylphosphinyl, or optionally substituted diphenylphosphinyl, for example diphenylphosphinyl.

Where the aforementioned hydroxy and amino groups are protected by an easily split off acyl radical, the acylating agent may be in the form of the free acid or a reactive functional derivative thereof, especially as mixed, or preferably simple, anhydride or as the acid halide, such as the acid chloride or bromide.

If the free acid is used for acylation, the reaction is usually carried out in the presence of suitable condensation agents, such as carbodiimides, for example N,N'-diethyl-, N,N'-dipropyl-, N,N'-dicyclohexyl- or N-ethyl-N'-3-dimethylaminopropyl-carbodiimide, suitable carbonyl compounds, for example carbonyldiimidazole, or 1,2-oxazolium compounds, such as 2-ethyl-5-phenyl-1,2-oxazolium-3'-sulfonate or 2-t-butyl-5-methyl-1,2-oxazolium perchlorate, or a suitable acylamino compound, for example 2-ethoxy-1-ethoxycarbonyl-1,2-dihydroquinoline. Alternatively, the reaction may be catalyzed in the presence of a strong acid, such as hydrogen chloride, sulfuric acid, and the like.

The condensation reaction is carried out preferably in an anhydrous reaction medium, preferably in the presence of a solvent or diluent, for example methylene chloride, dimethylformamide, acetonitrile or tetrahydrofuran, if desired or necessary while cooling or heating, for example within a temperature range of from approximately −40° C. to approximately +100° C., preferably from approximately −20° C. to approximately +50°, and/or in an inert gas atmosphere, for example a nitrogen atmosphere.

Where the protective acylation is performed using a corresponding acyl anhydride or acyl halide, the reaction is carried out preferably in the presence of an acid-binding agent, for example an organic base, such as an organic amine, for example a tertiary amine, such as tri-lower alkylamine, for example trimethylamine, triethylamine or ethyl-diisopropylamine, or N,N-di-lower alkylaniline, for example N,N-dimethylaniline, or a cyclic tertiary amine, such as an N-lower alkylated morpholine, such as N-methylmorpholine, or a base of the pyridine type, for example pyridine, or an inorganic base, for example an alkali metal or alkaline earth metal hydroxide, carbonate or bicarbonate, for example sodium potassium or calcium hydroxide, carbonate or bicarbonate under conditions well-known to the art.

Where the compounds of formulae III, V, VII or IX contain two adjacent phenolic hydroxy groups, e.g. where n is 2 and each $R_1$ is hydroxy in the 5- and 6-position respectively, these hydroxy groups may also be protected by forming the corresponding boric acid complex thereof by treating the compound with boric acid or a borate salt while maintaining a pH value of at least 7. Suitable borate salts include alkali metal metaborates, such as sodium metaborate, and alkali metal pentaborates, such as potassium pentaborate. Suitable solvents include water, and mixtures of water with an inert organic solvent, such as tetrahydrofuran, dioxane, or dimethylformormide, and is carried out at a temperature between about 0° and 70° C. in the presence of a base which may be organic, e.g. an amine base, such as pyridine or triethylamine, or inorganic, such as an alkali metal hydroxide including sodium hydroxide and potassium hydroxide, to provide a pH of between about 7 to 13.

Primary amino groups may also be protected by the formation of Schiff bases, by reaction of the amine group with an aldehyde or ketone to the corresponding imine. Suitable aldehydes include lower alkyl aldehydes, such as acetaldehyde and propionaldehyde, aryl aldehydes, such as benzaldehyde, di-lower alkyl ketones, such as acetone and 2-pentanone, and lower alkyl aryl ketones, such as acetophenone. Formation of the Schiff base may be accomplished at a temperature of between about 0° to about 100° C. in the presence of an inert diluent, such as a lower alkanol, such as ethanol or propanol or lower alkanoic acid, such as acetic acid, optionally in the presence of an inert atmosphere.

Carboxylic acid groups, such as those compounds wherein $R_2$ and/or $R_3$ are hydroxy or where $R_6$ is lower alkyl substituted by carboxy, may be protected by esterification, for example wherein the carboxy group is esterified by an aliphatic, cycloaliphatic, aromatic or araliphatic alcohol, for example a lower alkanol, such as ethanol or t-butyl alcohol or benzyl alcohol, or by a silyl or stannyl radical, such as tri-lower alkyl silyl or tri-lower alkyl stannyl, such as trimethyl-silyl or -stannyl.

The protective esterification of free carboxy groups may be accomplished by methods known per se. Thus, esterification may be accomplished using aliphatic diazo compounds or the aforementioned alcohols. Suitable aliphatic diazo compounds include diazomethane, diazoethane, diazo-n-butane and diphenyldiazomethane.

These reagents are employed in the presence of a suitable inert solvent, such as an aliphatic cycloaliphatic or aromatic hydrocarbon, such as hexane, cyclohexane, benzene or toluene, a halogenated aliphatic hydrocarbon, for example methylene chloride, or an ether, such as a di-lower alkyl ether, for example diethyl ether, or a cyclic ether, for example tetrahydrofuran or dioxan, or a solvent mixture, and, depending on the diazo reagent, while cooling, at room temperature or while slightly heating, and also, if necessary, in a closed vessel and/or under an inert gas atmosphere, for example a nitrogen atmosphere.

Where the free carboxy groups are protected by reaction with the aforementioned alcohols, the reaction may be carried out under the condition specified for the acylation of hydroxy groups with free carboxylic acids, set forth above.

Alternatively, the free carboxy groups to be protected may be converted to the corresponding mixed anhydride or acid halide, and subsequently reacted with the aforementioned aliphatic, cycloaliphatic, aromatic or araliphatic alcohols, especially a lower alkanol, using the reaction conditions specified above for protective acylation using an acyl anhydride or acyl halide. The free carboxy group to be protected in this alternative may be converted to the corresponding mixed anhydride by treating the acid (optionally having appropriately protected functional groups) or a suitable organic salt thereof, such as the pyridine or 4-methylmorpholine salt, or metal salt, such as the alkali metal salt, with a suitable acid derivative such as a corresponding acid halide of an optionally substituted lower alkanecarboxylic acid, such as trichloroacetyl chloride, or with a semiester of a carbonic acid semihalide, such as chloroformic acid ethyl ester, and the mixed anhydride so obtained can be used in the acylation reaction without isolation. This anhydride formation is advantageously conducted in an inert diluent, such as a lower alkyl ether, methylene chloride, toluene, dimethylformamide, dimethyl sulfoxide or the like, at a temperature between about 0° and 100° C., optionally in the presence of an inert atmosphere, e.g. nitrogen.

In a resulting compound of the formula I in which one or more functional groups are protected, these, for example protected carboxyl, amino and/or hydroxy groups, can be liberated, in a manner known per se, by means of solvolysis, especially hydrolysis, alcoholysis or acidolysis or by means of reduction, especially hydrogenolysis or chemical reduction, optionally stepwise or simultaneously.

Thus, t-lower alkoxycarbonyl, or lower alkoxycarbonyl substituted in the 2-position by an organic silyl group or in the 1-position by lower alkoxy or lower alkylthio, or optionally substituted diphenylmethoxycarbonyl can be converted into free carboxyl, for example by treating with a suitable acid, such as formic acid or trifluoroacetic acid, optionally with the addition of a nucleophilic compound, such as phenol or anisole. Optionally substituted benzyloxycarbonyl can be liberated, for example, by means of hydrogenolysis, i.e. by treating with hydrogen in the presence of a metallic hydrogenation catalyst, such as a palladium catalyst. Suitably substituted benzyloxycarbonyl, such as 4-nitrobenzyloxycarbonyl, can be converted into free carboxyl also by chemical reduction, for example by treating with an alkali metal dithionite, for example sodium dithionite, or with a reducing metal, for example zinc, or a metal salt, such as a chromium (II) salt, for example chromium (II) chloride, usually in the presence of a hydrogen-yielding agent which, together with the metal, is capable of producing nascent hydrogen, such as an acid, especially a suitable carboxylic acid, such as a lower alkanecarboxylic acid optionally substituted, for example by hydroxy, for example acetic acid, formic acid, glycolic acid, diphenylglycolic acid, lactic acid, mandelic acid, 4-chloromandelic acid or tartaric acid, or an alcohol or thiol, water preferably being added. By treatment with a reducing metal or metal salt as described above it is also possible to convert 2-halo-lower alkoxycarbonyl (optionally after converting a 2-bromo-lower alkoxycarbonyl group into a corresponding 2-iodo-lower alkoxycarbonyl group) or aroylmethoxycarbonyl into free carboxyl, aroylmethoxycarbonyl likewise being split off by treating with a nucleophilic, preferably salt-forming reagent, such as sodium thiophenolate or sodium iodide. Substituted 2-silylethoxycarbonyl can also be converted into free carboxyl by treating with a salt of hydrofluoric acid which yields the fluoride anion, such as an alkali metal fluoride, for example sodium or potassium fluoride, in the presence of macrocyclic polyether ("Crown ether"), or with a fluoride of an organic quaternary base, such as tetra-lower alkylammonium fluoride or tri-lower alkyl-aralkyl ammonium fluoride, for example tetraethylammonium fluoride or tetrabutylammonium fluoride, in the presence of an aprotic polar solvent, such as dimethyl sulphoxide or N,N-dimethylacetamide. A carboxyl group esterified by an organic silyl or stannyl group, such as tri-lower alkylsilyl or tri-lower alkylstannyl, for example trimethylsilyl, can be liberated in the usual manner by solvolysis, for example by treating with water, an alcohol or an acid.

A protected amino group is liberated in a manner known per se and, depending on the type of means of solvolysis or reduction. 2-Halo-lower alkoxy-carbonylamino (optionally after converting a 2-bromolower alkoxycarbonylamino group into a 2-iodo-lower alkoxycarbonylamino group), aroylmethoxycarbonylamino or 4-nitrobenzyloxycarbonylamino can be liberated, for example by treating with a suitable chemical reducing agent, such as zinc in the presence of a suitable carboxylic acid, such as aqueous acetic acid. Aroylmethoxy-carbonylamino can also be split by treating with a nucleophilic, preferably salt-forming, reagent, such as sodium thiophenolate, and 4-nitrobenzyloxy-carbonylamino also b.y treating with an alkali metal dithionite, for example sodium dithionite. Optionally substituted diphenylmethoxycarbonylamino, t-lower alkoxycarbonylamino or 2-tri-substituted silylethoxycarbonylamino can be liberated by treating with a suitable acid, for example formic or trifluoroacetic acid, optionally substituted benzyloxycarbonylamino, for example by means of hydrogenolysis, i.e. by treating with hydrogen in the presence of a suitable hydrogenation catalyst, such as a palladium catalyst, optionally substituted triarylmethylamino, formylamino or 2-acyl-lower alk-1-en-1-ylamino, for example by treating with an acid, such as a mineral acid, for example hydrochloric acid, or an organic acid, for example formic, acetic or trifluoroacetic acid, optionally in the presence of water, and an amino group protected by an organic silyl or stannyl group, for example by means of hydrolysis or alcoholysis. An amino group protected by 2-haloacetyl, for example 2-chloroacetyl, can be liberated by treating with thiourea in the presence of a base, or with a thiolate salt, such as an alkali metal thiolate, of thiourea, and by subsequent solvolysis, such as alcoholysis or hydrolysis, of the resulting condensation product. An amino group protected by 2-substituted silylethoxy carbonyl can also be converted into the free amino group by treating with a salt of hydrofluoric acid which yields fluoride anions, as stated above in connection with the liberation of a correspondingly protected carboxyl group. A phosphoramido, phosphonamido or phosphinamido group can be converted into the free amino group, for example by treating with phosphorus-containing acid, such as a phosphoric, phosphonic or phosphinic acid, for example orthophosphoric acid or polyphosphoric acid, an acid ester thereof, for example, monomethyl, monoethyl, dimethyl or diethyl phosphate, or monomethylphosphonic acid, or an anhydride thereof, such as phosphorus pentoxide.

A hydroxy group protected by a suitable acyl group, an organic silyl or stannyl group or by optionally substituted 1-phenyl-lower alkyl is liberated in the same manner as a correspondingly protected amino group. A hydroxy group protected by 2,2-dichloroacetyl is liberated, for example by basic hydrolysis, while a hydroxy group etherified by t-lower alkyl or by a 2-oxa- or 2-thia-aliphatic or a 2-oxa- or 2-thia-cycloaliphatic hydrocarbon radical is liberated, for example by treating with a mineral acid or a strong carboxylic acid, for example trifluoroacetic acid.

The described splitting reactions are carried out under conditions known per se, if necessary while cooling or heating, in a closed vessel and/or in an inert gas atmosphere, for example a nitrogen atmosphere.

When several protected functional groups are present, the protecting groups are preferably so chosen that more than one such group can be split off simultaneously, for example by acidolysis, such as by treating with trifluoroacetic acid or formic acid, or by reduction, such as by treating with zinc and acetic acid, or with hydrogen and a hydrogenation catalyst, such as a palladium-on-carbon catalyst.

Salts of compounds of the formula I having salt-forming groups can be manufactured in a manner known per se. Thus, salts of compounds of the formula I having acid groups can be formed, for example by treating with metal compounds, such as alkali metal salts of suitable organic carboxylic acids, for example the sodium salt of α-ethylcaproic acid or with inorganic alkali metal or alkaline earth metal salts, for example sodium hydroxide, carbonate or bicarbonate, or with ammonia or suitable organic amines, preferably stoichiometric quantities or only a small excess of the salt-forming agent being used. Acid addition salts of compounds of the formula I having basic group are obtained in the usual manner, for example by treating with an acid or a suitable anion exchange reagent. Internal salts of compounds of the formula I that contain, for example, a free carboxyl and a basic group can be formed, for example by neutralising salts, such as acid addition salts, to the isoelectric point, for example with weak bases, or by treating with liquid ion exchangers.

Salts can be converted in the usual manner into the free compounds; metal and ammonium salts can be converted, for example by treating with suitable acids reagents, and acid addition salts, for example by treating with a suitable basic agent.

The invention also relates to novel starting materials and processes for their manufacture.

The compounds of formula III are known, per se, or are easily derived from the known starting materials by those skilled in the art, as see, for example F. Weygand et al., *Ber.*, Vol. 89, p. 647 (1956); E. J. Corey et al., *J. Am. Chem. Soc.*, Vol. 92, p. 2496 (1970); U.S. Pat. No. 3,780,062 and U.S. Pat. No. 3,796,723.

The reactive functional derivatives of formula V are readily prepared from the compounds of formula III by reaction with the appropriate agent. Thus, the corresponding N-carbonyl chloride or thiocarbonyl chloride may be prepared by reacting the compounds of formula III (optionally with protected functional groups) with phosgene or thiophosgene in an inert diluent, such as toluene, methylene chloride, dimethylsulfoxide, di-lower alkyl ether or tetrahydrofuran, at a temperature of between −20° to 100° C. Advantageously, an excess of phosgene or thiophosgene is used.

The N-nitrile derivatives of formula V may be prepared by reacting a compound of formula III (optionally with protected functional groups) with cyanogen halides, such as cyanogen chloride or cyanogen bromide in an inert diluent, such as toluene or tetrahydrofuran at a temperature of between 0° and 100° C. The N-nitrile derivative of formula V may also be prepared by converting the compound of formula III (optionally with protected functional groups) to the corresponding 1-halo derivative by reaction with a hypohalite, such as an alkali metal hypohalite, e.g. sodium hypohalite, in ethereal solution, and reacting the corresponding haloamine formed with an alkali metal cyanide, such as potassium cyanide, optionally in the presence of an inert diluent, such as diethyl ether, tetrahydrofuran or dimethyl formamide, at a temperature between about 0° and 100° C.

The N-lower alkyl ester and thioester starting materials of formula V, may be prepared from the corresponding amines of formula III (optionally with protected functional groups) by reaction with phosgene or thiophosgene as set forth above, followed by reaction with a lower alkanol or lower alkyl mercaptan to yield the desired carbamic or thiocarbamic ester or thioester. This reaction is advantageously conducted in the presence of a tertiary amine, such as triethyl amine or pyridine, in an inert diluent, such as a lower alkyl ether or a di lower alkyl sulfoxide, at a temperature between about 0° and 100° C.

The lower alkyl imino ether and lower alkyl imino thioether reactive derivatives of formula V, are prepared conveniently by reaction of the compound of formula III (optionally with protected functional groups) with an isocyanate or isothiocyanate of the formula $R_7NCO$ or $R_7NCS$, respectively, or the corresponding carbamyl or thiocarbamyl halide, optionally in the presence of a base, such as triethylamine or pyridine to form the corresponding urea or thiourea, in an inert diluent, such as toluene, lower alkyl ethers, for example diethylether, or in tetrahydrofuran, dimethylsulfoxide or dioxane, at a temperature between 0° C. and 100° C., reacting the resulting urea or thiourea with a lower alkyl halide, preferably a methyl halide, or a lower alkyl sulfate, such as dimethyl sulfate, to form the corresponding lower alkyl, preferably methyl imino or iminothio ether, in a suitable diluent, such as water, an aqueous/lower alkanol mixture such as water/ethanol mixture or the like, at a temperature between about 0° and 100° C., preferably between about 10° and 80° C.

The reactive functional derivatives of compounds IV (optionally with protected function groups), are prepared analogously using the same techniques, from the amines of formula VI.

In addition, in those compounds of formula IV where $R_6$ is hydrogen, the corresponding reactive derivatives, in the form of the corresponding isocyanate or isothiocyanate (optionally in protected form) may be advantageously prepared from the corresponding compound of formula VI where $R_6$ is likewise hydrogen. Said isocyanate and isothiocyanate reactive derivatives of such compounds of formula IV are advantageously prepared from those compounds of formula VI (optionally with protected functional groups) where $R_6$ is hydrogen by methods known per se. One advantageous technique is to react such compounds of formula VI, preferably in the form of a hydrohalide salt thereof, with phosgene or thiophosgene to form the corresponding carbamyl chloride or thiocarbamyl chloride, in an inert diluent, such as toluene, methylene chloride, dimethylsulfoxide, di-lower alkyl ether, dioxane or tetrahydrofuran, at a temperature between −20° to 100° C., and dehydrohalogenating the resulting carbamyl chloride or thiocarbamyl chloride formed in situ with base, such as calcium hydroxide.

The compounds of formula VII are advantageously prepared by reacting a reactive functional derivative of formula V, such as an acid chloride, with an amine of the formula $R_6-NH_2$, in which optionally present functional groups in $R_1$, $R_2$ and $R_6$ are protected, in the presence of an inert solvent or diluent, such as benzene, toluene, tetrahydrofuran and the like, at a temperature between about −20° to 100° C., optionally under a nitrogen atmosphere.

The compounds of formula VII may also be prepared by reacting a compound of formula III with a reactive functional derivative of a compound of the formula X

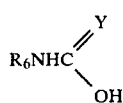

(X)

wherein any functional groups in R<sub>6</sub> may be protected.

The compounds of formula IX are prepared, inter alia, by reacting known indole compounds of the formula

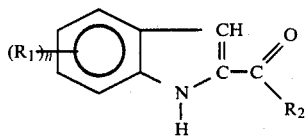

(XI)

with a reactive functional derivative of a compound of formula IV, in which optionally functional groups may be in protected form in accordance with the procedure and techniques set forth above for the reaction between the compounds of formula III and said functional derivatives of the compounds of formula IV. Alternatively, one may prepare the indole analogs of the reactive functional derivatives of the indoline compounds of the formula V from the compounds of formula XI, using the procedures and techniques set forth above for the preparation of the derivatives of formula V, and react said indole analogs with a compound of formula VI in accordance with the techniques and procedures set forth above for the reaction of the reactive derivatives of the compound of formula V and VI, to obtain the indole compounds of formula IX.

Starting materials of formula XII may be prepared by processes 1 to 5 herein wherein the reactants of formulae III to IX and XI are replaced with the corresponding nitriles, e.g. the reactants in which the groups $COR_2$ and/or $COR_3$ are replaced by $C \equiv N$. The nitriles thus obtained may be converted to the carboxylic acids, esters and amides of formula I using methods well known to the art.

With reference to the above reactions involving the reactants of formulae III through XII, the expression "optionally in protected form" is understood to mean appropriately protecting potentially reactive amino, hydroxy and carboxy substituents in accordance with the protective techniques set forth above, such that interfering reactions are avoided, by protecting such substituents prior to the desired reaction and subsequently, if necessary, removing the protective groups to obtain the desired compounds, e.g. of formula I.

The invention further includes any variant of said processes, in which an intermediate product obtainable at any stage of the process is used as a starting material and any remaining steps are carried out, or the process is discontinued at any stage thereof, or in which the starting materials are formed under the reaction condition, or in which the reaction components are used in the form of their salts or optically pure antipodes.

In case diastereomeric mixtures of the above compounds of Formulae I to IX and XII are obtained, these can be separated into the single racemic or optically active diastereomers by methods in themselves known, e.g., by fractional distillation, crystallization and/or chromatography. Racemic products can likewise be resolved into the optical antipodes, for example, by separation of diastereomeric salts thereof, such as according to J. Org. Chem. 43, 3803 (1978), e.g., by the fractional crystallization of d- or l-(tartrates, mandelates, camphorsulfonates, or 1-naphthyl-1-ethylisocyanates) of compounds having a basic salt-forming group, or of d- or l-(α-methylbenzylamine, cinchonidine, cinchonine, quinine, quinidine, ephedrine, dehydroabietylamine, brucine or strychnine)-salts of compounds having an acidic salt-forming group. The preferred starting material of Formula III is the 2-S-optical isomer (epimer) thereof.

Advantageously, for carrying out the processes according to the invention, those starting substances that lead to the initially specially mentioned groups of final products and especially to the specially described or emphasized final products are used.

The present invention additionally relates to the compounds of the formula I and their pharmaceutically acceptable, non-toxic acid addition salts for use as medicaments, especially as hypotensive, antihypertensive and cardioactive agents, for example for the treatment of raised blood pressure and especially to their use for the preparation of pharmaceutical preparations, especially preparations having an antihypertensive action.

The present invention also relates to pharmaceutical e.g., cardiovascular preparations that contain compounds of the formula I or pharmaceutically acceptable acid addition salts of such compounds. The pharmaceutical preparations according to the invention are for enteral administration, such as oral or rectal administration, and for parenteral administration, and the preparations contain the pharmacological active substance alone or together with a pharmaceutically acceptable carrier.

The new pharmaceutical preparations contain from approximately 10% to approximately 95%, preferably from approximately 20% to approximately 90% of the active substance. Pharmaceutical preparations according to the invention in dosage unit form are, for example, dragees, tablets, capsules, suppositories or ampoules. The pharmaceutical preparations of the present invention are prepared in a manner known per se, for example by means of conventional mixing, granulating, dragee-making, dissolving or lyophilizing processes.

Thus, pharmaceutical preparations for oral use may be obtained by combining the active substance with solid carriers and, optionally, adjuncts, optionally granulating a resulting mixture and procesing the mixture or granulate, if desired or necessary after the addition of suitable adjuncts, to form tablets or dragee cores.

Suitable carriers are especially fillers, such as sugars, for example lactose, saccharose, mannitol or sorbitol, cellulose preparations and/or calcium phosphates, for example tri-calcium phosphate or calcium hydrogen phosphate; also binders, such as starch pastes prepared, for example, using maize, wheat rice, or potato starches, gelatin, tragacanth, methylcellulose, hydroxypropylmethylcellulose, sodium carboxymethylcellulose and/or polyvinylpyrrolidone; and, if desired, disintegrators, such as the above-mentioned starches; furthermore, carboxymethyl starches, transversely cross-linked polyvinylpyrrolidone, agar, alginic acid or a salt thereof, such as sodium alginate. Adjuncts are especially flow regulators and lubricants, for example silica, talc, stearic acid or salts thereof, such as magnesium or calcium stearate, and/or polyethylene glycol. Dragee cores are provided with suitable coatings that may be resistant to gastric juice, for which there are used, inter alia, concentrated sugar solutions that optionally contain gum arabic, talc, polyvinylpyrrolidone, polyethylene glycol and/or titanium dioxide, lacquer solutions in suitable organic solvents or solvent mixtures, or, for the preparation of coatings resistant to gastric juice, solutions of suitable cellulose preparations, such as acetylcellulose phthalate or hydroxypropylmethylcellulose phthalate. Colourants or pigments may be added to the tablets or dragee coatings, for example to identify or characterize different doses of active substance.

Other pharmaceutical preparations that may be administered orally are dry-filled capsules made of gelatin, and also soft, sealed capsules consisting of gelatin and plasticiser, such as glycerin or sorbitol. The dry-filled capsules may contain the active substance in the form of a granulate, for example in admixture with fillers, such as lactose, binders, such as starches, and/or lubricants, such as lactose, binders, such as starches, and/or lubricants, such as talc or magnesium stearate, an optionally stabilisers. In soft capsules, the active substance is preferably dissolved or suspended in suitable liquids, such as fatty oils, paraffin oil or liquid polyethylene glycols, and stabilizers may likewise be added.

Pharmaceutical preparations for rectal administration are, for example, in the form of suppositories consisting of a combination of the active substance and a suppository base substance. Suitable base substances for suppositories are, for example, natural or synthetic triglycerides, paraffin hydrocarbons, polyethylene glycols and higher alkanols. It is also possible to use gelatin rectal capsules that contain a combination of the active substance and a base substance. Suitable base substances are, for example, liquid triglycerides, polyethylene glycols and paraffin hydrocarbons.

For parenteral administration, aqueous solutions of an active substance in water-soluble form, for example in the form of a water-soluble salt, are especially suitable; also suitable are suspensions of the active substance, such as corresponding oily injection suspensions, for which suitable lipophilic solvents or vehicles, such as fatty oils, for example sesame oil, or synthetic fatty acid esters, for example ethyl oleate or triglycerides, are used; or aqueous injection suspensions that contain substances increasing viscosity, for example sodium carboxymethylcellulose, sorbitol and/or dextran and, optionally, stabilizers.

The invention likewise relates to the method of treatment of cardiovascular diseases, especially hypertension, using the compounds of the formula I or pharmaceutically acceptable, non-toxic salts of such compounds as pharmacologically active substances, especially as anti-hypertensive agents, preferably in the form of pharmaceutical preparations. The dosage of active substance administered is dependent on the species of warm-blooded animal, the body weight, age and individual condition, and on the form of administration. The daily dose administered to a warm-blooded animal of about 70 kg body weight is, on average, from approximately 25 to approximately 400 mg of active substance.

The following examples illustrate the above-described invention; however, they are not intended to restrict its scope in any way whatsoever. Temperatures are given in degrees Centigrade. If not mentioned otherwise, all evaporations are performed under reduced pressure, preferablly between about 15 and 100 mm Hg. Unless stated otherwise optical rotations are measured in methanol at room temperature.

As illustrated in the examples, the preferred diastereomers, e.g., the indoline-2S-chiral epimers of formula II wherein the carbon atom to which $R_5$ is attached has been assigned the R-configuration, are usually characterized as:

(a) the less polar diastereomers on the basis of chromatographic migration (e.g. column or thin layer chromatography on silica gel), and (b) the diastereomers with the lowest negative optical rotation.

EXAMPLE 1

Into a suspension of 1 g of ethyl 2,3-dihydroindole-2S-carboxylate hydrochloride in 10 ml of toluene, phosgene was bubbled until all solids dissolved. The mixture was refluxed for 2 hours while bubbling of phosgene continued. The mixture was then evaporated to dryness under aspirator pressure. The oily residue was dissolved in 5 ml of methylene chloride and the solution of ethyl N-chlorocarbonyl-2,3-dihydroindole-2-carboxylate was added dropwise to a solution of 1.19 g of ethyl 2-methylaminomethyl-4-phenylbutyrate hydrochloride, 0.89 g of triethylamine in 20 ml of methylene chloride with stirring and cooling at 0° C. The mixture was stirred at 0° C. for ½ hour, stored at 5° C. overnight, washed with 1N hydrochloric acid, water, dried over MgSO₄, and evaporated. The residue was chromatographed on 60 g of silica gel using ethyl acetate-methylene chloride (1:9) as eluent to give ethyl 1(S)-[(R,S)-N-(2-ethoxycarbonyl-4-phenyl butyl)-N-methylcarbamoyl]-2,3-dihydroindole-2-carboxylate having $[\alpha]_D^{25} = -53.09°$, as a mixture of diastereomers.

The starting materials were prepared as follows.

(a) ethyl α-(phenethyl)acrylate (also called ethyl 2-methylene-4-phenylbutanoate was prepared according to the method described in the Bull. Soc. Chim. Fr. (1970), 219–30.

To a solution of 3.6 g of methylamine in 240 ml of ethanol 24.09 g of ethyl α-(phenethyl) acrylate was added at once and the mixture was kept at room temperature for 7 days. The ethanol was evaporated at aspirator pressure and, the residue was taken up in ether and extracted four times with 25 ml of 2N hydrochloric acid. The aqueous extracts were basified with 2N sodium hydroxide and extracted four times with ether. The ether extracts were washed with water, dried over MgS₀₄, evaporated to dryness and the residue was distilled at high vacuum to give ethyl 2-methylaminomethyl-4-phenylbutyrate, bp. 125°–128°/1 mm Hg, m.p. 80°–2° for the corresponding hydrochloride salt prepared under standard conditions.

(b) 120 g of 1-Acetylindoline-2-carboxylic acid [Nippon Kagaku Zasshi 87, 760 (1966)] and 172 g of l-cinchonidine were dissolved in 1,200 ml of hot ethanol. The solution was allowed to stand at room temperature overnight and then at 0° for 4 days. The white crystalline salt was filtered off and discarded. The filtrate was evaporated, 1,000 ml of water were added and the solution was adjusted to pH=1 with concentrated hydrochloric acid. After 15 minutes the product was collected by filtration and washed thrice with 250 ml of 2N aqueous hydrochloric acid, twice with 500 ml of water and twice with 100 ml of ethanol, to give the 1-acetylindoline-2S-carboxylic acid melting at 214°–215°; $[\alpha]_D = -133.3°$ (C.=1.165 in ethanol).

The suspension of 37.5 g thereof in 380 ml of 2N aqueous hydrochloric acid was deoxygenated by bubbling nitrogen through it for 5 minutes, followed by refluxing for 2 hours. It was cooled to room temperature, filtered through infusorial earth, the filtrate evaporated and the residue crystallized from diethyl ether-isopropanol, to yield the indoline-2S-carboxylic acid hydrochloride melting at 133° (dec.); $[\alpha]_D = -70.4$ (c=1 in ethanol).

The solution of 34 g thereof in 350 ml of ethanol was saturated with dry hydrogen chloride without external cooling. The mixture was stirred for 2 hours at room temperature and the solvent removed until crystallization begins. The concentrate was poured into 400 ml of diethyl ether, cooled at 0° for 1 hour and filtered, to yield the indoline-2S-carboxylic acid ethyl ester hydrochloride melting at 179°–181°;$[\alpha]_D = -63°$ (c=1.385 in ethanol).

EXAMPLE 2

In accordance with the reaction method of Example 1, ethyl 2-ethylaminomethyl-4-phenylbutyrate hydrochloride was reacted with ethyl N-chlorcarbonyl-2,3-dihydroindole-2S-carboxylate.

The resulting diastereomeric mixture of ethyl 1(S)-[(R,S)-N-(2-ethoxycarbonyl-4-phenylbutyl)-N-ethylcarbamoyl]-2,3-dihydro indole-2-carboxylates was separated by column chromatography on silica gel using ethyl acetate-methylene chloride (5:95) to give the less polar ethyl 1(S)-[(R)-N-(2-ethoxycarbonyl-4-phenylbutyl)-N-ethylcarbamoyl]-2,3-dihydroindole-2-carboxylate having $[\alpha]_D^{25} = -45.81°$, and the more polar ethyl 1(S)-[(S)-N-(2-ethoxycarbonyl-4-phenylbutyl)-N-ethylcarbamoyl]-2,3-dihydroindole-2-carboxylate having $[\alpha]_D^{25} = -61.83°$.

Ethyl 2-ethylaminomethyl-4-phenylbutyrate, b.p. 128°/1 mm Hg, was prepared from ethyl α-(phenethyl)acrylate and ethylamine by the procedure described for the corresponding 2-methylaminomethyl-4-phenylbutyrate of Example 1.

EXAMPLE 3

A solution of 1.85 g of ethyl 1(S)-[(R,S)-N-(2-ethoxycarbonyl-4-phenylbutyl)-N-methylcarbamoyl]-2,3-dihydroindole-2-carboxylate of Example 1 in 30 ml of methanol was cooled to 0° and 8.22 ml of 1N sodium hydroxide were added dropwise with stirring. The mixture was stirred at room temperature overnight and evaporated at aspirator pressure. The residue was triturated with acetone-ether, the mixture was stirred at room temperature for several hours and filtered to give 1(S)-[(R,S)-N-(2-carboxy-4-phenylbutyl)-N-methylcarbamoyl]-2,3-dihydroindole-2-carboxylic acid disodium salt having $[\alpha]_D^{25} = -44.09°$, as a mixture of diastereomers.

EXAMPLE 4

In a similar manner as described in Example 3 were prepared 1(S)-[(R)-N-(2-carboxy-4-phenylbutyl)-N-ethylcarbamoyl]-2,3-dihydroindole-2-carboxylic acid disodium salt having $[\alpha]_D^{25} = -45.99°$; and 1(S)-[(S)-N-(2-carboxy-4-phenylbutyl)-N-ethylcarbamoyl]-2,3-dihydroindole-2-carboxylic acid disodium salt having $[\alpha]_D^{25} = -59.13°$, using the products of Example 2.

EXAMPLE 5

To a solution of 2.3 g of ethyl 2-(S)-[(R)-N-(2-ethoxycarbonyl-4-phenylbutyl)-N-ethylcarbamoyl]-2,3-dihydroindole-2-carboxylate of Example 2 in 5 ml of ethanol was added 5 ml of 2N sodium hydroxide. The mixture was stirred for 4 hours at room temperature. The mixture was neutralized with 10 ml of 1N hydrochloric acid and extracted 5 times with ethyl ether. The ether extracts were washed with water, brine, dried and evaporated to give 1(S)-[(R)-N-(2-ethoxycarbonyl-4-phenylbutyl)-N-ethylcarbamoyl]-2,3-dihydroindole-2-carboxylic acid having $[\alpha]_D^{25} = -5.23°$.

EXAMPLE 6

Essentially following the above procedures of examples 1–4, were prepared the following compounds of formula II having the indoline-2S-chiral configuration wherein $R_1$ represents hydrogen and $R_5$ represents $CH_2CH_2C_6H_5$.

| Compound | $R_2$ | $R_3$ | $R_6$ | $CHR_5$ Configuration | Salt | $[\alpha]_D$ |
|---|---|---|---|---|---|---|
| 6/a | OC$_2$H$_5$ | OC$_2$H$_5$ | CH$_2$CH$_2$OH | R | — | −28.59° |
| 6/b | OC$_2$H$_5$ | OC$_2$H$_5$ | CH$_2$CH$_2$OH | S | — | −34.38° |
| 6/c | OH | OH | CH$_2$CH$_2$OH | R | diNa | −44.64° |
| 6/d | OH | OH | CH$_2$CH$_2$OH | S | diNa | −55.39° |
| 6/e | OC$_2$H$_5$ | OC$_2$H$_5$ | CH(CH$_3$)$_2$ | R | — | −21.15° |
| 6/f | OC$_2$H$_5$ | OC$_2$H$_5$ | CH(CH$_3$)$_2$ | S | — | −32.67° |
| 6/g | OH | OH | CH(CH$_3$)$_2$ | R | diNa | −39.46° |
| 6/h | OH | OH | CH(CH$_3$)$_2$ | S | diNa | −77.65° |

The initial product prepared according to example 1 and consisting of a mixture of diastereomers 6/a and 6/b or 6/e and 6/f respectively was separated into the pure diastereomers by high pressure liquid chromatography.

Compounds 6/c, 6/d and 6/h were isolated as hydrates containing 1.5 moles of water.

The starting material ethyl 2-hydroxyethylaminomethyl-4-phenylbutyrate, b.p. 165°–172°/1 mm Hg, for compounds 6/a to 6/d was prepared from ethyl α-(phenethyl)acrylate and β-hydroxy ethylamine.

The starting ethyl 2-isopropylaminomethyl-4-phenylbutyrate for compounds 6/e to 6/h was similarly prepared.

EXAMPLE 7

Ethyl 1(S)-[(R,S)-N-(2-ethoxycarbonyl-4-phenylbutyl)-N-(4-benzyloxycarbonylaminobutyl)carbamoyl]-2,3-dihydroindole-2-carboxylate, as a mixture of diastereomers, was prepared from ethyl 2-(4-benzyloxycarbonylaminobutyl)aminomethyl-4-phenylbutyrate and ethyl N-chlorocarbonyl-2,3-dihydroindole-2-carboxylate according to the method of Example 1.

The diastereomers were separated by preparative high pressure liquid chromatography (HPLC) with toluene-methylene chloride, 9:1 as eluent to give the less polar ethyl 1(S)-[(R)-N-(2-ethoxycarbonyl-4-phenylbutyl)-N-(4-benzyloxycarbonylaminobutyl)carbamoyl]-2,3-dihydroindole-2-carboxylate having $[\alpha]_D^{25} = -39.25°$ and the more polar ethyl 1(S)-[(S)-(2-ethoxycarbonyl-4-phenylbutyl)-N-(4-benzyloxycarbonylaminobutyl)carbamoyl]-2,3-dihydroindole-2-carboxylate having $[\alpha]_D^{25} = -44.13°$.

The starting material, ethyl 2-(4-benzyloxycarbonylaminobutyl)aminomethyl-4-phenylbutyrate was prepared as follows:

To a solution of 147 g of 1,4-diaminobutane in 490 ml of methylene chloride, a solution of 41 ml of benzyl chloroformate in 84 ml of methylene chloride was added dropwise at 0° over a period of 1 hour. The mixture was stirred at 0° for 1 hour, then washed twice with water and extracted four times with 150 ml of 4N hydrochloric acid. The acidic extracts were washed with methylene chloride, basified with 450 ml of 22% of sodium hydroxide and extracted four times with methylene chloride. The organic extracts were dried over magnesium sulfate and evaporated to give 4-benzyloxycarbonylamino-1-butylamine, having NMR peaks at δ=7.3, 5.05 and 2.6 ppm.

A mixture of 20 g of 4-benzyloxycarbonylamino-1-butylamine, 21.04 g of ethyl α-(phenethyl)acrylate and 200 ml of ethanol was stirred at room temperature for 8 days and evaporated to dryness. The residue was dissolved in ethyl ether and the solution was extracted three times with 100 ml of 2N hydrochloric acid. The aqueous layer was basified with 2N sodium hydroxide and extracted three times with methylene chloride, dried over magnesium sulfate and evaporated to give the ethyl 2-(4-benzyloxycarbonylaminobutyl)aminomethyl-4-phenylbutyrate having signals in the NMR spectrum at δ=7.4, 7.25, and 5.1 ppm.

EXAMPLE 8

A solution of 1.6 g of ethyl 1(S)-[(R)-N-(2-ethoxycarbonyl-4-phenylbutyl)-N-(4-benzyloxycarbonylaminobutyl)carbamoyl]-2,3-dihydroindole-2-carboxylate in 16 ml of ethanol and 0.2 ml of acetic acid is hydrogenated over 0.16 g of 10% Palladium on Carbon at room temperature and atmospheric pressure. The catalyst is filtered and the filtrate is evaporated to dryness. The residue is dissolved methylene chloride and the solution is washed with 10% aq. potassium carbonate, water, then dried over magnesium sulfate and evaporated to give ethyl 1(S)-[(R)-N-(2-ethoxycarbonyl-4-phenylbutyl)-N-(4-aminobutyl)carbamoyl]-2,3-dihydroindole-2-carboxylate having $[\alpha]_D^{25} = -45.48°$.

In a similar manner, hydrogenation of ethyl 1(S)-[(S)-N-(2-ethoxycarbonyl-4-phenylbutyl)-N-(4-benzyloxycarbonylaminobutyl)carbamoyl]-2,3-dihydroindole-2-carboxylate gave ethyl 1(S)-[(S)-N-(2-ethoxycarbonyl-4-phenylbutyl)-N-(4-aminobutyl) carbamoyl]-2,3-dihydroindole-2-carboxylate having $[\alpha]_D^{25} = -53.59°$.

EXAMPLE 9

1(S)-[(R)-N-(2-Carboxy-4-phenylbutyl)-N-(4-aminobutyl) carbamoyl]-2,3-dihydroindole-2-carboxylic acid disodium salt was prepared from the corresponding (S,R)-diastereomeric diester of example 8, according to the reaction method of Example 3, having $[\alpha]_D^{25} = -47.22°$.

Similarly hydrolysis of the (S,S)-diastereomeric diester of example 8 gave 1(S)-[(S)-N-(2-carboxy-4-phenylbutyl)-N-(4-aminobutyl)carbamoyl]-2,3-dihydroindole-2-carboxylic acid disodium salt having $[\alpha]_D^{25} = -56.75°$.

EXAMPLE 10

Hydrolysis of ethyl 1(S)-[(R)-N-(2-ethoxycarbonyl-4-phenylbutyl)-N-(4-aminobutyl)carbamoyl]-2,3-dihydroindole-2-carboxylate according to the procedure of example 5 gave 1(S)-[(R-N-(2-ethoxycarbonyl-4-phenylbutyl)-N-(4-aminobutyl)carbamoyl]-2,3-dihydroindole-2-carboxylic acid having an $[\alpha]_D^{25} = -46.56°$.

EXAMPLE 11

The mixture of 3.82 g of ethyl 2,3-dihydroindole-2S-carboxylate hydrochloride, 85.5 ml of methylene chloride and 3.3 g of triethylamine is cooled to 0° and a solution of 5 g of N-methyl-N-(2-ethoxycarbonyl-4-phenylbutyl)carbamoyl chloride in methylene chloride is added dropwise over a period of 10 minutes with stirring. The mixture is kept at room temperature overnight, washed with 1N hydrochloric acid, water, dried over MgSO4 and evaporated to give ethyl 1(S)-[(R,S)-N-(2-ethoxycarbonyl-4-phenylbutyl)-N-methylcarbamoyl]-2,3-dihydroindole-2-carboxylate of example 1.

The starting material was prepared as follows:

To a solution of 10.3 g of phosgene in 45 ml of toluene, the solution of 20.3 g of ethyl 2-methylaminomethyl-4-phenylbutyrate (described in example 1) in 19 ml of toluene was added over a period of 20 minutes. The mixture was stirred at room temperature for 4 hours and evaporated to dryness. The residue was stirred for 10 minutes with 100 ml of ether, the solids were filtered, the filtrates were evaporated to dryness and the residue was distilled under high vacuum to give N-methyl-N-(2-ethoxycarbonyl-4-phenylbutyl)carbamoyl chloride, bp 179°-189°/1 mm Hg.

EXAMPLE 12

Essentially following the procedures of the foregoing examples the following compounds of formula II can be prepared.

| Compound | $R_5$ | $R_6$ | $R_1$ | $R_2$ | $R_3$ |
|---|---|---|---|---|---|
| 12/a | $CH_2CH_2p$-$ClC_6H_5$ | $CH_3$ | H | OH | $OC_2H_5$ |
| 12/b | $CH_3$ | $CH_3$ | H | OH | OH |
| 12/c | $CH_2CH_2C_6H_5$ | $C_2H_5$ | 5-$CH_3$ | OH | OH |
| 12/d | $CH_2CH_2C_6H_5$ | $(CH_2)_4NH_2$ | 5-$OCH_3$ | OH | OH |
| 12/e | $CH_2CH_2C_6H_5$ | $(CH_2)_4NH_2$ | 5-Cl | OH | OH |

Preparation of starting material for compound 12/b:

To a solution of 12.4 g of methylamine in 45 ml of methanol was added with stirring and ice-water cooling a solution of 60.2 g of methyl 2-methylacrylate in 40 ml of methanol over a period of 1 hour. The mixture was allowed to stand at room temperature for 3 days, was evaporated and the residue was distilled at aspirator pressure to give the methyl 2-methyl-3-methylaminopropionate, bp. 57°-59° C./15 mm Hg.

To a solution of 16 g of phosgene in 70 ml of toluene, a solution of 17.4 g of methyl 2-methyl-3-methylaminopropionate in 30 ml of toluene was added dropwise with stirring at 20° C. The mixture was stirred at room temperature for 4 hours and evaporated to dryness. The residue was stirred for 10 min. with 100 ml of ethyl ether, filtered, the filtrates are evaporated to dryness and the residue was distilled at high vacuum to give the N-methyl-N-(2-methoxycarbonylpropyl)carbamoyl chloride, bp. 97°-100°/1 mm Hg.

EXAMPLE 13

Preparation of 10,000 tablets each containing 10 mg of the active ingredient of Example 5:

Formula:

| | |
|---|---|
| 1-(S)—[(R)-N—(2-ethoxycarbonyl-4-phenyl-butyl)-N—ethylcarbamoyl]-2,3-dihydroindole-2-carboxylic acid | 100.00 g |
| Lactose | 1,157.00 g |
| Corn Starch | 75.00 g |
| Polyethylene glycol 6,000 | 75.00 g |
| Talcum powder | 5.00 g |
| Magnesium stearate | 18.00 g |

-continued

| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 14

Preparation of 10,000 capsules each containing 10 mg of the active ingredient of Example 10:

Formula:

| | |
|---|---|
| 1(S)—[(R)-N—(2-ethoxycarbonyl-4-phenylbutyl)-N—(4-aminobutyl)carbamoyl]-2,3-dihydroindole-2-carboxylic acid | 100.0 g |
| Lactose | 1,800.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine.

Analogously tablets or capsules are prepared from the remaining compounds of the invention, e.g., those illustrated by the examples herein.

What is claimed is:

1. A compound being 1(S)-[(R)-N-(2-ethoxycarbonyl-4-phenylbutyl)-N-(4-aminobutyl)carbamoyl]-2,3-dihydroindole-2-carboxylic acid or a pharmaceutically acceptable salt thereof.

2. A pharmaceutical composition comprising an angiotensin-converting enzyme inhibiting compound of claim 1 and a pharmaceutically acceptable carrier.

3. A method for treating cardiovascular diseases responsive to angiotensin-converting enzyme inhibition which comprises adminstering to a mammal in need thereof an effective angiotensin-converting enzyme inhibitory amount of a compound of claim 1 or of a pharmaceutical composition comprising a said compound.

4. A compound being 1(S)-[(R)-N-(2-carboxy-4-phenylbutyl)-N-(4-aminobutyl)carbamoyl]-2,3-dihydroindole-2-carboxylic acid or a pharmaceutically acceptable salt thereof.

5. A pharmaceutical composition comprising an angiotensin-converting enzyme inhibiting compound of claim 4 and a pharmaceutically acceptable carrier.

6. A method for treating cardiovascular diseases responsive to angiotensin-converting enzyme inhibition which comprises administering to a mammal in need thereof an effective angiotensin-converting enzyme inhibiting amount of a compound of claim 4 or of a pharmaceutical composition comprising a said compound.

7. A compound being 1(S)-[(S)-N-(2-carboxy-4-phenylbutyl)-N-(4-aminobutyl)carbamoyl]-2,3-dihydroindole-2-carboxylic acid or a pharmaceutically acceptable salt thereof.

8. A pharmaceutical composition comprising an angiotensin-converting enzyme inhibiting compound of claim 7 and a pharmacetically acceptable carrier.

9. A method for treating cardiovascular diseases responsive to angiotensin-converting enzyme inhibition which comprises adminstering to a mammal in need thereof an effective angiotensin-converting enzyme inhibitory amount of a compound of claim 7 or of a pharmaceutical composition comprising a said compound.

* * * * *